United States Patent [19]

Staetz et al.

[11] Patent Number: 5,472,700
[45] Date of Patent: * Dec. 5, 1995

[54] COMBINATIONS OF NEEM SEED EXTRACT AND BIFENTHRIN FOR CONTROL OF ECTOPARASITES ON ANIMALS

[75] Inventors: Charles A. Staetz, Newtown; H. Robinson Ertelt, West Chester, both of Pa.; Gert P. Volpp, Princeton, N.J.

[73] Assignee: FMC Corporation, Philadelphia, Pa.

[*] Notice: The portion of the term of this patent subsequent to Oct. 4, 2011, has been disclaimed.

[21] Appl. No.: 317,262

[22] Filed: Oct. 3, 1994

Related U.S. Application Data

[63] Continuation-in-part of Ser. No. 139,252, Oct. 20, 1993, Pat. No. 5,352,672.

[51] Int. Cl.$^6$ .................................................. A01N 25/00
[52] U.S. Cl. .................................... 424/405; 424/DIG. 8
[58] Field of Search .............................. 424/405, DIG. 8

[56] References Cited

U.S. PATENT DOCUMENTS

| | | | |
|---|---|---|---|
| 4,238,505 | 12/1980 | Engel | 424/305 |
| 5,352,672 | 10/1994 | Staetz et al. | 514/65 |
| 5,372,817 | 12/1994 | Locke et al. | 424/405 |

FOREIGN PATENT DOCUMENTS

| | | |
|---|---|---|
| 89213283 | 1/1989 | Australia . |
| 89165860 | 4/1989 | Australia . |

OTHER PUBLICATIONS

Abstract: Synergistic effect of insecticides—NOE mixture on the mortality of mosquito. Culex quinquefasciatus. Sci. Cult. 1990 56(8) 340–2.

*Primary Examiner*—Thurman K. Page
*Assistant Examiner*—William E. Benston, Jr.
*Attorney, Agent, or Firm*—H. Robinson Ertelt; Robert M. Kennedy

[57] ABSTRACT

Combinations of bifenthrin with azadirachtin-containing neem seed extracts are synergistic in controlling acarids, especially pyrethroid-resistant mites, over a wide range of azadirachtin to bifenthrin ratios. The combinations are also used for the control of ectoparasites on animals.

4 Claims, No Drawings

COMBINATIONS OF NEEM SEED EXTRACT AND BIFENTHRIN FOR CONTROL OF ECTOPARASITES ON ANIMALS

This is a continuation-in-part of application Ser. No. 139,252, filed Oct. 20, 1993, now U.S. Pat. No. 5,352,672.

The present invention relates to methods for controlling acarids and insects. In particular, it relates to the application of combinations of bifenthrin and an extract from seeds of the African/Asian neem tree (*Azadirachta indica*) to the locus where control of acarids or insects is desired, including the control of ectoparasites on animals. The combination has been found especially effective in the control of pyrethroid-resistant mites.

Bifenthrin is a known pyrethroid insecticide. Neem seed extract, a complex mixture including several bioactive compounds, has long been known to have insecticidal and insect feeding inhibition properties, generally attributed to the compound azadirachtin. Synergistic interactions have been reported for different neem extracts with a variety of materials, including piperonyl butoxide, common vegetable oils, and several different insecticides, including pyrethrins and synthetic pyrethroids. However, combinations of pyrethroids with neem extracts are not always synergistic. Synergism is shown by Qadri and Rao (Pesticides (Bombay), 14(3), 11, 1980), who report a combination of pyrethrins and neem seed extract is more effective against certain household and stored products pests than would be expected from the individual contributions of the components. A brochure issued by AgriDyne Technologies Inc. suggests possible synergism between a neem seed extract and s-fenvalerate against cabbage looper. On the other hand, Samuthiravelu and David (The Madras Agricultural Journal, 77, 294, 1990) report that combinations of deltamethrin and neem seed extract are no better at controlling the spotted boll worm on cotton than is deltamethrin alone. Other publications suggest using neem extracts in combination with pyrethrins or pyrethroids to control insects, not necessarily for any possible synergism, but for their different modes of action. No report of synergism against acarids has been found.

The only report found in which bifenthrin and a neem seed extract were used in combination is in a second brochure issued by AgriDyne Technologies Inc. In that brochure several insecticides, both alone and in combination with Azatin™ insecticide, a neem seed extract containing 3.0% azadirachtin, are tested for control of the sweetpotato whitefly. However, from the information presented it is not possible to tell if the combination of Azatin with bifenthrin is better than bifenthrin alone.

Neither bifenthrin nor the neem extracts, when applied alone at the rates tested, control pyrethroid-resistant twospotted spider mite. The efficacy of the apparent synergistic combination of these two known insecticides against this species is heretofore unknown.

Bifenthrin, which is known to be effective against a broad range of foliar-feeding pests, is described in U.S. Pat. No. 4,238,505 and has the following structure

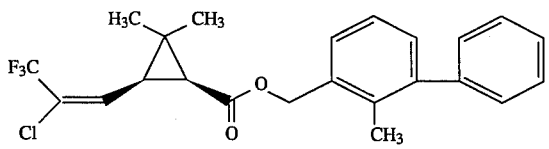

Azadirachtin, an organic molecule belonging to a class of compounds known as tetranortriterpenoids, to which the insecticidal activity of neem extract is commonly attributed, has the following structure:

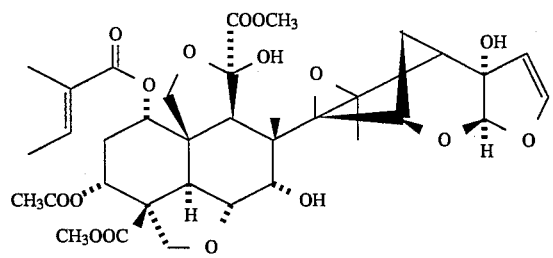

Azadirachtin is known to interfere with insect molting, reproduction, and digestion.

It has now been found that combinations of bifenthrin and azadirachtin-containing neem seed extracts are synergistic in their control of pyrethroid-resistant twospotted spider mites over a wide range of ratios. Surprisingly, these combinations appear somewhat antagonistic in their control of a strain of twospotted spider mite susceptible to pyrethroids.

Bifenthrin, azadirachtin, and the combinations were tested against both susceptible and pyrethroid-resistant twospotted spider mite (*Tetranychus urticae*). In these tests, the compounds were tested as technical materials or as formulations. The technical materials were tested as 10% acetone/water solutions (v/v) containing 0.1% of the surfactant octylphenoxypolyethoxyethanol. The formulated materials were tested as water solutions.

Bifenthrin was tested as a technical material and as a 2 EC formulation (an emulsifiable concentrate containing 2.0 lb of technical bifenthrin (95% active ingredient) per gallon of formulation). A typical 2 EC formulation of bifenthrin consists of (weight/weight) 26.53% technical bifenthrin, 7.51% emulsifiers, and 65.96% inert diluent and solvent.

Technical neem seed extract was a solid material containing 15.9% azadirachtin, as analyzed by HPLC. This solid was obtained from Agridyne Technologies Inc., 417 Wakara Way, Salt Lake City, Utah 84108. The identities of the remaining components of this solid extract were not determined.

One neem seed extract formulation used in these tests was Margosan-O®, Botanical Insecticide Concentrate (Grace Sierra Crop Protection Co., 1001 Yosemite Dr., Milpitas, Calif. 95035),an ethanol extract of neem tree seeds containing about 3000 ppm (0.3% ai) of azadirachtin and about 20% neem oil, to which has been added polyoxyethylene sorbitan monolaurate or octylphenoxypolyethoxyethanol (emulsifiers), and adjusted to pH 4.0 with ammonium hydroxide.

Another neem seed extract formulation used in these tests was Azatin™ Insecticide (obtained from Agridyne Technologies Inc.). This formulation contains about 3.0% azadirachtin, 27% other neem plant compounds, and 70% inert ingredients that one would find in a typical emulsifiable concentrate formulation.

For the tests against the twospotted spider mites, a 100×15 mm polystyrene petri dish for each of two replicates of each rate of application was lined with a cotton pad. The cotton pad was moistened with about 10–15 mL of distilled water. Three leaf discs, each 2.5 cm in diameter, were punched from the leaves of a lima bean plant (*Phaseolus lunatus*) and placed bottom side up on the cotton pad in each dish. Each disc was infested with about 10–15 adult female mites with the aid of a microscope and a small artist's brush.

A hand-held DeVilbiss sprayer was used to spray the discs at 5–10 psi with a test solution of the appropriate concentration until the leaf surfaces were evenly covered with the spray solution. The combinations of bifenthrin and azadirachtin were sprayed as mixtures. The discs were allowed to dry for about 1–2 hours. The petri dishes containing the discs were then covered with their lids and placed in a growth chamber, where they were maintained for a 72-hour exposure period at 24° C. and 50% relative humidity and a light/dark cycle of 15 hr/9 hr. Mortality counts were taken after the 72 hours of exposure time. The results reported in each Table are side-by-side tests, so as to minimize the variability inherent in tests on living organisms.

Table 1 shows the results of tests on pyrethroid-susceptible mites. It is clear that there is no synergism, and in fact the two materials appear antagonistic.

Tables 2 through 7 show a variety of tests with technical neem seed extract and the two neem extract formulations, where the concentration is given in terms of azadirachtin content, and technical bifenthrin and formulated bifenthrin. Table 2, in which technical materials are used, shows synergism over a bifenthrin to azadirachtin ratio of 4:1 to 4000:1! In Tables 3 and 4 two different concentrations of bifenthrin and a narrower range of azadirachtin concentrations were used. Synergism is shown for each combination tested. Table 4 is similar to Table 3, except that formulated extract is used rather than technical. Tables 3 and 4 show synergism over a range of 400:1 to 20:3. Tables 5 and 6 show synergism over a wider range of bifenthrin concentrations with two neem extract concentrations. Table 6 repeats the concentrations of Table 5, but with each component as a formulation, with the demonstrated bifenthrin to azadirachtin synergism range 540:1 to 54:3. Table 7 extends the bifenthrin/azadirachtin ratio to 3:10.

Combinations of bifenthrin and azadirachtin are also effective in animal health use for the control of ectoparasites. Ectoparasites, such as acarids and some species of flies, can cause a variety of animal health problems, not only causing discomfort to the animal, but in the case of animals raised for food or fiber resulting in economic loss. Representative ectoparasites include cattle ticks, dog ticks, poultry mites, horn flies and face flies.

Control of ectoparasites on animals by the combinations of this invention is illustrated by the application to cattle infested with horn fly (*Haematobia irritans*) with aqueous solutions containing bifenthrin as the sole active ingredient, azadirachtin as the sole active ingredient, and bifenthrin and azadirachtin in combination. For example, an emulsifiable concentrate of bifenthrin was diluted to give aqueous solutions containing in one case 25 ppm of bifenthrin, in another, 12.5 ppm of bifenthrin. An emulsifiable concentrate of Azatin™ insecticide was diluted to give an aqueous solution containing 100 ppm of azadirachtin. Similarly, aqueous solutions were prepared containing in one case 25 ppm of bifenthrin and 100 ppm of azadirachtin, in another 12.5 ppm of bifenthrin and 100 ppm of azadirachtin. Each of these solutions was sprayed on cattle naturally infested with horn fly.

Another example of the use of the combination in animal health is to prevent infestation of cattle by the southern cattle tick (*Boophilus microplus*). The aqueous solutions used in this example contained 25 ppm of bifenthrin for bifenthrin alone, 100 ppm of azadirachtin for azadirachtin alone, and 25 ppm of bifenthrin and 100 ppm of azadirachtin for the combination. Again, the application to the cattle was by spraying.

In summary, in different tests at different times, synergism has been demonstrated for combinations of three different azadirachtin-containing neem seed extracts with technical and formulated bifenthrin over a range of ratios of bifenthrin to azadirachtin of 4000:1 to 3:10, with a great number of intermediate ratios. Combinations of azadirachtin-containing neem seed extracts with bifenthrin have been applied to cattle for the control of horn fly at ratios of bifenthrin to azadirachtin of 1:4 and 1:8 and for the control of ticks at a ratio of bifenthrin to azadirachtin of 1:4.

In normal use the bifenthrin/neem seed extract combinations of the present invention usually will not be employed free from admixture or dilution, but ordinarily will be used in a suitable formulated composition compatible with the method of application and comprising an acaricidally or insecticidally effective amount of the combination. The combinations of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present bifenthrin/neem seed extract combinations may be applied, for example, as sprays, dusts, or granules to the area where pest control is desired, the type of application varying, of course, with the pest and the environment. Thus, the combinations of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the combinations. The granule particles are relatively large, a diameter of about 400–2500 microns typically. The particles are either impregnated with the combination from solution or coated with the combination, adhesive sometimes being employed. Granules generally contain 0.05–10%, preferably 0.5–5%, active ingredient as the acaricidally effective amount.

Dusts are admixtures of the combinations with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling acarids contains 1 part of the synergistic combination and 99 parts of talc.

The synergistic combinations of the present invention may be made into liquid concentrates by dissolution or emulsification in suitable liquids and into solid concentrates by admixture with talc, clays, and other known solid carriers used in the pesticide art. The concentrates are compositions containing, as an acaricidally effective amount, about 5–50% of the combination and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Useful liquid concentrates include the emulsifiable concentrates, which are homogeneous liquid or paste compositions readily dispersed in water or other liquid carriers. They may consist entirely of a concentrate of a combination of the invention with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the acaricidal composition.

Other useful formulations include simple solutions of the active ingredient in a solvent in which it is completely soluble at the desired concentrations, such as acetone or other organic solvents.

It is apparent that various modifications may be made in the formulation and application of the synergistic combinations of this invention without departing from the inventive concepts herein as defined in the claims.

TABLE 1

Tests on Twospotted Spider Mite (Pyrethroid-Susceptible)

| | | % Mortality | | |
|---|---|---|---|---|
| | Rate | Single | A (1.3 ppm) + B | |
| Component | (ppm) | Component | Expected | Observed |
| Bifenthrin (A) | 1.3 | 48 | — | — |
| Extract (B) | 1000 | 92 | 100 | 91 |
| Extract | 100 | 19 | 67 | 72 |
| Extract | 10 | 15 | 63 | 38 |
| Extract | 1 | 14 | 62 | 36 |

(A) is technical bifenthrin
(B) is neem seed extract containing 15.9% azadirachtin, tested at indicated ppm of azadirachtin

TABLE 2

Tests on Twospotted Spider Mite (Pyrethroid-Resistant)

| | | % Mortality | | |
|---|---|---|---|---|
| | Rate | Single | A (400 ppm) + B | |
| Component | (ppm) | Component | Expected | Observed |
| Bifenthrin (A) | 400 | 52 | — | — |
| Extract (B) | 1000 | 65 | 100 | 100 |
| Extract | 100 | 20 | 72 | 91 |
| Extract | 10 | 17 | 69 | 90 |
| Extract | 1 | 18 | 70 | 90 |
| Extract | 0.1 | 10 | 62 | 92 |

(A) is technical bifenthrin
(B) is neem seed extract containing 15.9% azadirachtin, tested at indicated ppm of azadirachtin

TABLE 3

Tests on Twospotted Spider Mite (Pyrethroid-Resistant)

| | | % Mortality | | | | |
|---|---|---|---|---|---|---|
| | Rate | Single | A (400 ppm) + B | | A (200 ppm) + B | |
| Component | (ppm) | Component | Expected | Observed | Expected | Observed |
| Bifenthrin (A) | 400 | 52 | — | — | — | — |
| Bifenthrin | 200 | 23 | — | — | — | — |
| Extract (B) | 30 | 5 | 57 | 96 | 28 | 91 |
| Extract | 10 | 6 | 58 | 93 | 29 | 82 |
| Extract | 3 | 1 | 53 | 95 | 24 | 83 |
| Extract | 1 | 0 | 52 | 86 | 23 | 63 |

(A) is technical bifenthrin
(B) is neem seed extract containing 15.9% azadirachtin, tested at indicated ppm of azadirachtin

TABLE 4

Tests on Twospotted Spider Mite (Pyrethroid-Resistant)

| | | % Mortality | | | | |
|---|---|---|---|---|---|---|
| | Rate | Single | A (400 ppm) + C | | A (200 ppm) + C | |
| Component | (ppm) | Component | Expected | Observed | Expected | Observed |
| Bifenthrin (A) | 400 | 52 | — | — | — | — |
| Bifenthrin | 200 | 23 | — | — | — | — |
| Extract (C) | 30 | 51 | 100 | 100 | 74 | 98 |
| Extract | 10 | 2 | 49 | 95 | 25 | 96 |
| Extract | 3 | 6 | 53 | 90 | 29 | 86 |
| Extract | 1 | 6 | 53 | 88 | 29 | 69 |

TABLE 4-continued

Tests on Twospotted Spider Mite (Pyrethroid-Resistant)

| | | % Mortality | | | | |
|---|---|---|---|---|---|---|
| | Rate | Single | A (400 ppm) + C | | A (200 ppm) + C | |
| Component | (ppm) | Component | Expected | Observed | Expected | Observed |

(A) is technical bifenthrin
(C) Margosan-O ® insecticide is a neem seed extract containing 0.3% azadirachtin, tested at indicated ppm of azadirachtin

TABLE 5

Tests on Twospotted Spider Mite (Pyrethroid-Resistant)

| | | % Mortality | | | | |
|---|---|---|---|---|---|---|
| | Rate | Single | B (10 ppm) + A | | B (1 ppm) + A | |
| Component | (ppm) | Component | Expected | Observed | Expected | Observed |
| Extract (B) | 10 | 0 | — | — | — | — |
| Extract | 1 | 1 | — | — | — | — |
| Bifenthrin (A) | 1000 | 96 | 96 | 98 | 97 | 94 |
| | 540 | 69 | 69 | 91 | 70 | 93 |
| | 300 | 58 | 58 | 98 | 59 | 98 |
| | 100 | 52 | 52 | 84 | 53 | 89 |
| | 30 | 8 | 8 | 82 | 9 | 78 |

(A) is technical bifenthrin
(B) is neem seed extract containing 15.9% azadirachtin, tested at indicated ppm of azadirachtin

TABLE 6

Tests on Twospotted Spider Mite (Pyrethroid-Resistant)

| | | % Mortality | | | | |
|---|---|---|---|---|---|---|
| | Rate | Single | C (10 ppm) + D | | C (1 ppm) + D | |
| Component | (ppm) | Component | Expected | Observed | Expected | Observed |
| Extract (C) | 10 | 85 | — | — | — | — |
| Extract | 1 | 0 | — | — | — | — |
| Bifenthrin (D) | 1000 | 100 | 100 | 100 | 100 | 100 |
| | 540 | 74 | 100 | 98 | 74 | 98 |
| | 300 | 56 | 100 | 95 | 56 | 96 |
| | 100 | 49 | 100 | 86 | 49 | 86 |
| | 30 | 0 | 85 | 97 | 0 | 65 |

(C) Margosan-O ® insecticide is a neem seed extract containing 0.3% azadirachtin, tested at indicated ppm of azadirachtin
(D) an emulsifiable concentrate containing 2.0 pounds of technical bifenthrin per gallon of formulation, tested at indicated ppm bifenthrin.

TABLE 7

Tests on Twospotted Spider Mite (Pyrethroid-Resistant)

| Component | Rate (ppm) | Single Expected | Observed | Expected | Observed | Expected | Observed |
|---|---|---|---|---|---|---|---|
| | | | A (30 ppm) + B | | A (10 ppm) + B | | A (3 ppm) + B |
| Extract (B) | 10 | 7 | 10 | 92 | 8 | 98 | 7 | 89 |
| Extract | 1 | 6 | 9 | 89 | 7 | 82 | 6 | 67 |
| Bifenthrin (A) | 30 | 3 | | | | | |
| Bifenthrin | 10 | 1 | | | | | |
| Bifenthrin | 3 | 0 | | | | | |

TABLE 7-continued

Tests on Twospotted Spider Mite (Pyrethroid-Resistant)

| Component | Rate (ppm) | Single Expected | D (30 ppm) + | | D (10 ppm) + | | D (3 ppm) + | |
|---|---|---|---|---|---|---|---|---|
| | | | Observed | Expected | Observed | Expected | Observed | Expected |
| Extract (C) | 10 | 58 | 62 | 98 | 61 | 98 | 65 | 85 |
| Extract (C) | 1 | 0 | 4 | 91 | 3 | 93 | 7 | 79 |
| Extract (E) | 10 | 16 | 20 | 95 | 19 | 92 | 23 | 85 |
| Extract (E) | 1 | 5 | 9 | 91 | 8 | 91 | 12 | 79 |
| Bifenthrin (D) | 30 | 4 | | | | | | |
| Bifenthrin | 10 | 3 | | | | | | |
| Bifenthrin | 3 | 7 | | | | | | |

(A) is technical bifenthrin
(B) is neem seed extract containing 15.9% azadirachtin, tested at indicated ppm of azadirachtin
(C) Margosan-O ® insecticide is a neem seed extract containing 0.3% azadirachtin, tested at indicated ppm of azadirachtin
(D) an emulsifiable concentrate containing 2.0 pounds of technical bifenthrin per gallon of formulation, tested at indicated ppm bifenthrin
(E) Azatin™ insecticide is a neem seed extract containing 3.0 azadirachtin, tested at indicated ppm azadirachtin.

We claim:

1. A method of controlling ectoparasites on animals which comprises applying to the animals on which control is desired a parsiticidally effective amount of azadirachtin-containing neem seed extract and bifenthrin, the ratio of azadirachtin to bifenthrin being in the range of 8 to 1 to 1 to 4000.

2. A method of claim 1 in which the ectoparasites are ticks or mites.

3. A method of controlling ectoparasites on animal which comprises applying to the animals on which control is desired a parasiticidally effective amount of a composition containing an azadirachtin-containing neem seed extract and bifenthrin, the ratio of azadirachtin to bifenthrin being in the range of 4 to 1 to 1 to 1000.

4. A method of claim 3 in which the ectoparasites are ticks or mites.

* * * * *